United States Patent [19]
Gabbay

[11] Patent Number: 6,099,551
[45] Date of Patent: Aug. 8, 2000

[54] PERICARDIAL STRIP AND STAPLER ASSEMBLY FOR DIVIDING AND SEALING VISCERAL TISSUES AND METHOD OF USE THEREOF

[75] Inventor: Shlomo Gabbay, Short Hills, N.J.

[73] Assignee: Shelhigh, Inc., Millburn, N.J.

[21] Appl. No.: 09/141,978

[22] Filed: Aug. 28, 1998

Related U.S. Application Data

[63] Continuation-in-part of application No. 09/041,091, Mar. 12, 1998.

[51] Int. Cl.[7] .......................... A61B 17/08; A61B 17/068
[52] U.S. Cl. .............................................. 606/219; 227/176
[58] Field of Search ...................... 606/219, 220, 606/139, 144, 151; 227/178.1, 179, 177, 180, 180.1, 176.1

[56] References Cited

U.S. PATENT DOCUMENTS

| | | |
|---|---|---|
| 4,930,674 | 6/1990 | Barak . |
| 5,116,349 | 5/1992 | Aranyi . |
| 5,141,144 | 8/1992 | Foslien et al. . |
| 5,263,629 | 11/1993 | Trumbull et al. . |
| 5,368,599 | 11/1994 | Hirsch et al. . |
| 5,397,324 | 3/1995 | Carroll et al. . |
| 5,441,193 | 8/1995 | Gravener . |
| 5,503,638 | 4/1996 | Cooper et al. . |
| 5,542,594 | 8/1996 | McKean et al. . |
| 5,549,628 | 8/1996 | Cooper et al. . |
| 5,575,803 | 11/1996 | Cooper et al. . |
| 5,662,259 | 9/1997 | Yoon ...................................... 606/219 X |

OTHER PUBLICATIONS

"Bovine Pericardium Versus Bovine Collagen to Buttress Staples for Lung Reduction Operations", Richard J. Fischel, MD PhD, and Robert J. McKenna, Jr., MD, pp. 217–219.
"Reinforced staple line in severely emphysematous lungs", *J Thorac Cardiovasc Surg*, 1989;97:362–3.
"The Annals of Thoracic Surgery", *Official Journal of the Society of Thoracic Surgeons and the Southern Thoracic Surgical Association*, vol. 57, No. 4, Apr. 1994, pp. 1038–1039.
Advertisement for "Seamguard Staple Line Reinforcement Material", W. L. Gore & Associates, Inc., bearing copyright notice of 1996.

*Primary Examiner*—Michael Buiz
*Assistant Examiner*—Vikki Trinh
*Attorney, Agent, or Firm*—Amin, Eschweiler & Turocy, LLP

[57] ABSTRACT

A pericardial strip and surgical stapler assembly, and method of use thereof, in which at least one pericardial strip is releasably attached to the jaws of the stapler by passing the outer ends of the stapler through holes in the strip(s). Preferably, the trailing end(s) of the strip(s) are secured to the proximal ends of the jaws by O-ring(s), suture(s) attached to the trailing end of the strip(s), or opening(s) in the strip(s). When the tissue is cut, the O-ring(s), suture(s), or opening(s) are also cut, thus permitting removal of the stapler and allowing at least a portion of the pericardial strips to remain.

31 Claims, 5 Drawing Sheets

PERICARDIAL STRIP AND STAPLER ASSEMBLY FOR DIVIDING AND SEALING VISCERAL TISSUES AND METHOD OF USE THEREOF

This Application is a Continuation-in-Part of application Ser. No. 09/041,091, filed Mar. 12, 1998.

The present Invention is directed to the surgical incision of visceral tissues of warm blooded animals, especially resection of all or a portion of the human lung. Although the following description will focus on lung tissue, the Invention is applicable to visceral tissues of virtually all types.

BACKGROUND OF THE INVENTION

It has been known to use stapling devices to seal visceral tissue upon resection thereof. However, stapling of the lungs often results in an air leak which is detrimental to the health of the patient. This is especially true when the resection is used to accomplish "lung reduction". Since the lung reserves of such patients are very limited, even a small air leak can be extremely detrimental and even fatal.

In order to minimize the foregoing problem, pericardial tissue has been used in conjunction with a surgical stapler. Typically, the pericardial tissue is retained on the jaws by a cloth or plastic sleeve. However, this makes the procedure cumbersome and awkward. The foregoing is particularly true if the procedure is endoscopic.

The surgical stapler comprises three principal parts. One contains the staples, the other constitutes an anvil which receives the staples and initiates bending them in the proper direction, and the third, which is optional, is the knife which puts the final bend on the staples and cuts the tissue where desired.

Surgical staplers usually are designed to insert two rows of staples, spaced apart from each other in a direction perpendicular to the longitudinal axis of their jaws. In such a case, the knife cuts between the two rows.

SUMMARY OF THE INVENTION

In order to solve the foregoing problem, the present Invention eliminates the cloth or plastic sleeve. This is accomplished by using a pericardial strip and surgical stapler assembly wherein the strips are provided with an opening adjacent their leading ends. The intermediate section extends from the leading end to the trailing end remote therefrom. The openings in the pericardial strips are placed over the distal ends of the two jaws of the stapler. This retains the leading ends of the strips on the jaws. In addition, in a preferred form of the Invention, the trailing ends of the strips are secured to the proximal ends of the jaws by an O-ring, also preferably made of pericardial tissue. In an alternative form of the Invention, the trailing ends of the strips are provided with sutures whereby the surgeon can manually tie them to the jaws.

In a second embodiment of the Invention, the pericardial strip has a hole adjacent the trailing end. Thus, the distal end of the jaw of the stapler enters the hole and the trailing end is slid to a point adjacent the proximal end thereof. Then, the opening at the leading end is slipped over the distal end of the jaw, thereby securing the strip thereto at both ends. This eliminates the necessity for the O-ring.

Once the assembly has been inserted and the visceral tissue which is to be cut placed between the jaws, the stapler is actuated and it drives the—preferably double—row of staples through the two pericardial strips and the tissue against an anvil which initiates bending of the staples. Thereafter, the knife both cuts the tissue as desired and bends the staples further so that they are permanently attached. At the same time, this will sever the O-ring or the sutures so that the stapler may be readily removed and the pericardial strips left behind to seal the lung. In place of the O-ring, there can be provided suitable sutures which are applied manually by the surgeon. In those cases in which the stapler is not provided with a knife, it is removed after the staples have been driven and surgical scissors or another instrument is used to cut the tissue and the O-ring or sutures.

BRIEF DESCRIPTION OF THE DRAWINGS

In the accompanying drawings, constituting a part hereof and in which like reference characters indicate like parts.

DETAILED DESCRIPTION OF THE INVENTION

Figures 1, 2, 3, 4:
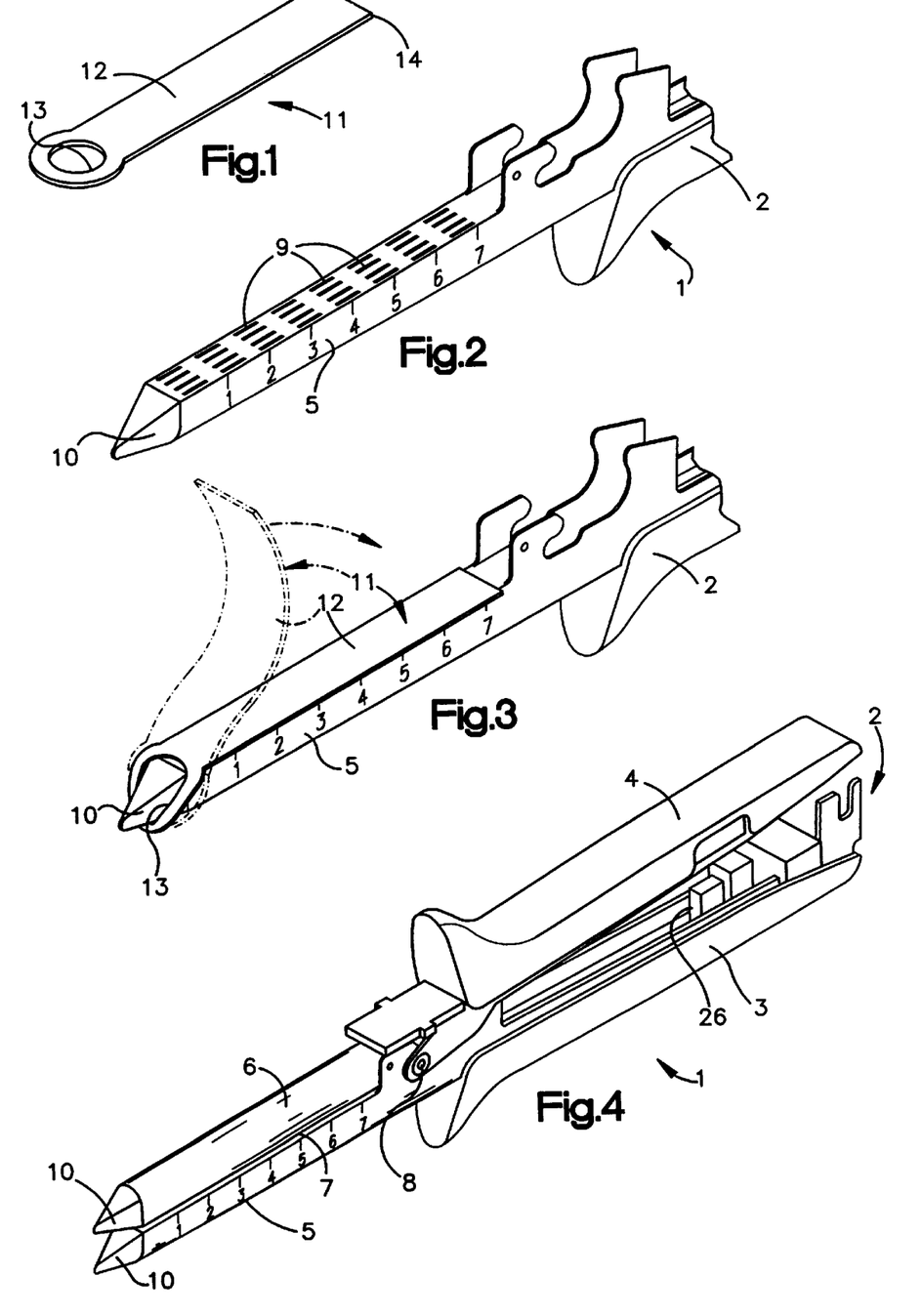
FIG. 1 is a plan view of the pericardial strip.
FIG. 2 is a schematic view of one jaw of a surgical stapler.
FIG. 3 is a schematic perspective view showing the pericardial strip fully attached in solid lines and partially attached in broken lines.
FIG. 4 is a perspective view of a typical surgical stapler as used in the present Invention.

Surgical stapler 1, as shown in FIGS. 2 and 4, comprises handle 2, first jaw 5, and second jaw 6. Handle 2 consists of stationary part 3 and movable part 4. The staples (not shown) are stored in first jaw 5 and anvil 7 is provided on second jaw 6 to receive the staples and initiate bending thereof. Staple holes 9 are provided on first jaw 5 and distal end 10 is preferably pointed for ease of insertion.

Pericardial strip 11 consists of a leading end having opening 13 and intermediate portion 12 extending to trailing end 14. As shown in FIG. 3, opening 13 is placed over end 10 so that the leading end of pericardial strip 11 is releasably secured to jaw 5. As shown in solid lines, pericardial strip 11 is secured to jaw 5.

Figures 5, 6, 7:
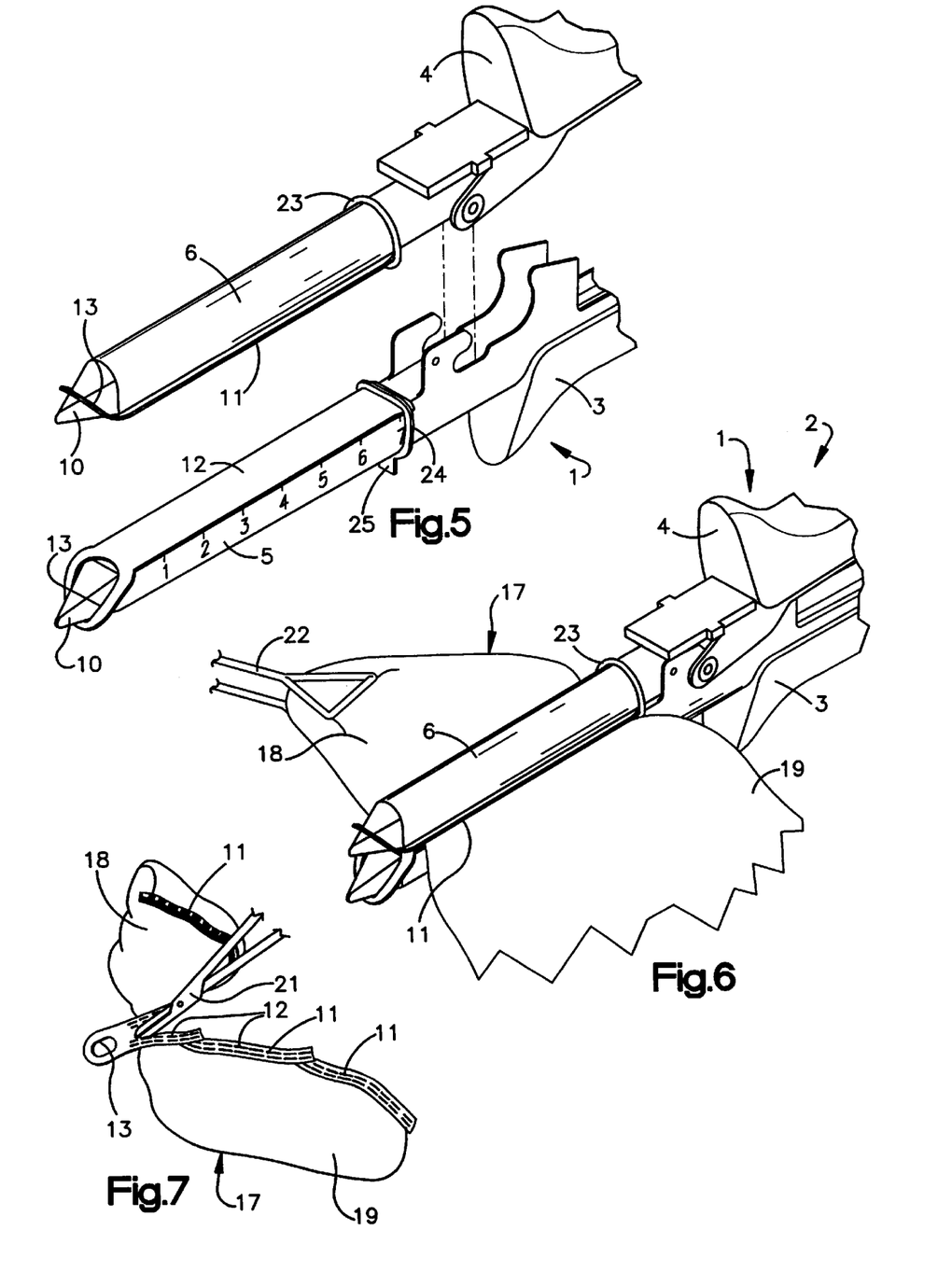
FIG. 5 is a schematic partial view of the jaws of a surgical stapler with the pericardial strips attached.
FIG. 6 shows the surgical stapler being applied to visceral tissue.
FIG. 7 is a view, similar to that of FIG. 6, wherein surgical scissors are cutting the visceral tissue.

The operation of the assembly is shown in FIGS. 5 to 7. Openings 13 of pericardial strips 11 have been placed over ends 10 of jaws 5 and 6 of the surgical stapler. The trailing ends are secured by O-rings 23 or 24, shown in FIGS. 9 and 10. Such rings would come in two sizes, one of which would preferably carry an indicium, such as tab 25, so that the surgeon can readily distinguish between the sizes. Alternatively, sutures 15 (FIG. 8) can be used in place of O-rings 23 or 24. Movable part 4 is rotated about pivot 8 (FIG. 4) so that second jaw 6 is adjacent first jaw 5 with lung 17 therebetween. Actuator 26 causes the staples to be driven through pericardial strips 11 and lung 17. Surgical scissors 21 are used to cut lung 17 into excised portion 18 and retained portion 19. The former is removed by forceps 22.

The leading ends of pericardial strips 11 may be removed along with excised portion 18 or, at the option of the surgeon, left in place. Thus, the incision line is sealed so that no air leaks occur.

Figures 8, 9, 10, 11:
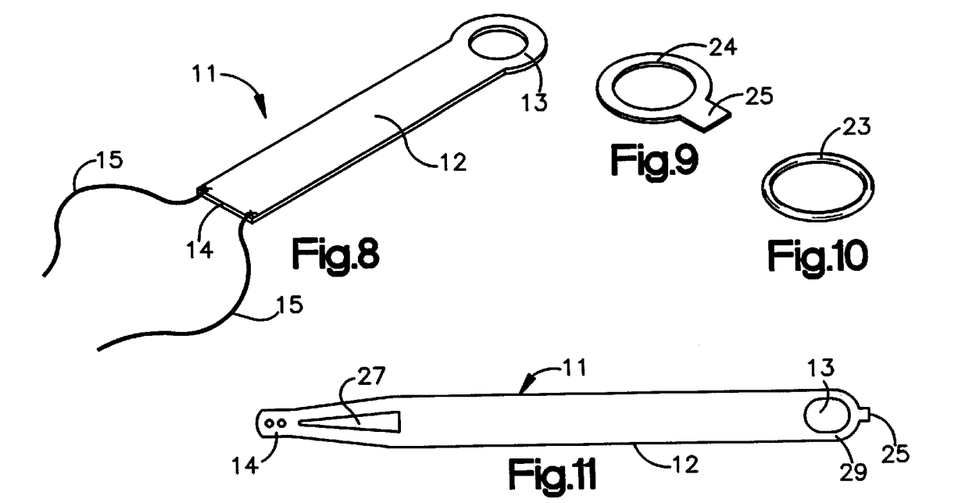
FIG. 8 is a view, similar to that of FIG. 1, showing the sutures attached to the trailing end of the pericardial strip.
FIG. 9 is a plan view of one form of O-ring.
FIG. 10 is a view, similar to that of FIG. 9, of a second form of O-ring.
FIG. 11 is a plan view of the second embodiment of the pericardial strip of the present Invention.
Figure 12:
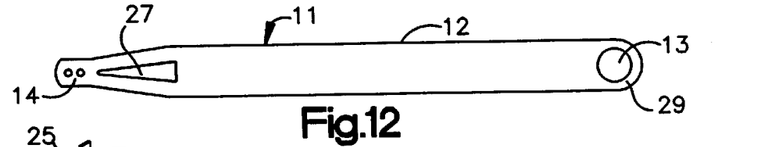
FIG. 12 is similar to FIG. 2 and shows a modification of the pericardial strip.

Referring now to FIG. 8, a modification of pericardial strip 11 is shown. It carries the same opening 13 and flat intermediate section 12 as does the device of FIG. 1. However, at trailing end 14, sutures 15 are attached. This makes it convenient for the surgeon to tie the trailing end to jaw 5 or 6 of stapler 1. When lung 17 is cut, sutures 15 are also cut, thereby allowing end 10 of surgical stapler 1 to be slipped out of opening 13 and removed.

Figure 13:
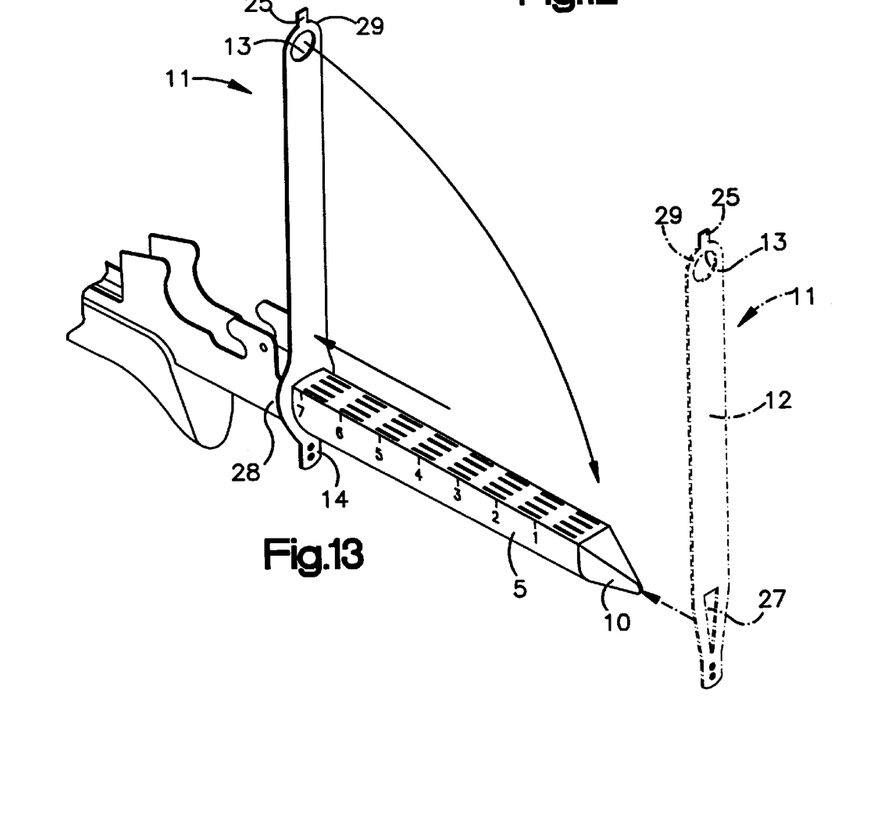
FIG. 13 is a perspective view, showing the insertion of the trailing end of the pericardial strip of FIG. 12.
Figure 14:
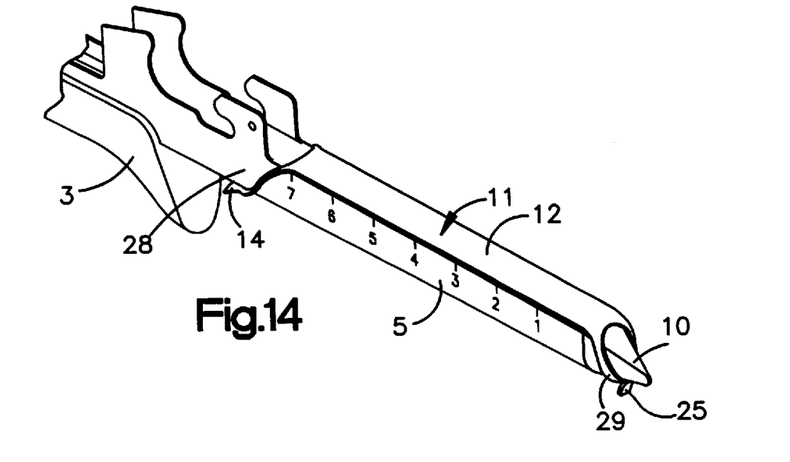
FIG. 14 is a view, similar to that of FIG. 3, showing the pericardial strip on a jaw of the stapler.
Figure 15:
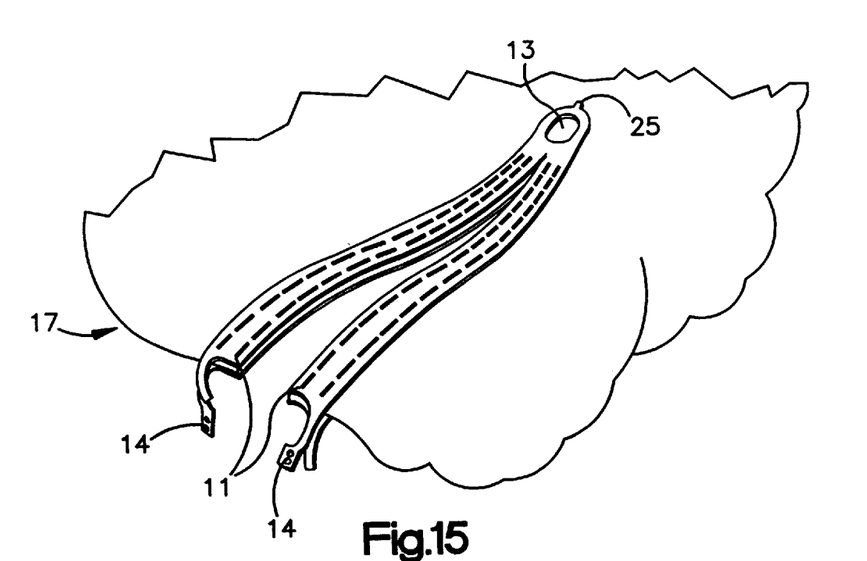
FIG. 15 is a view showing the pericardial strips on the visceral tissue.
Figure 16:
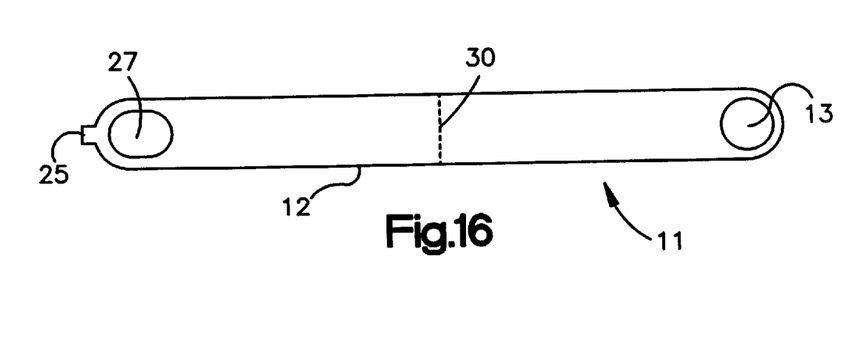
FIG. 16 is a view, similar to that of FIG. 11, of a third embodiment of the present Invention.
Figure 17:
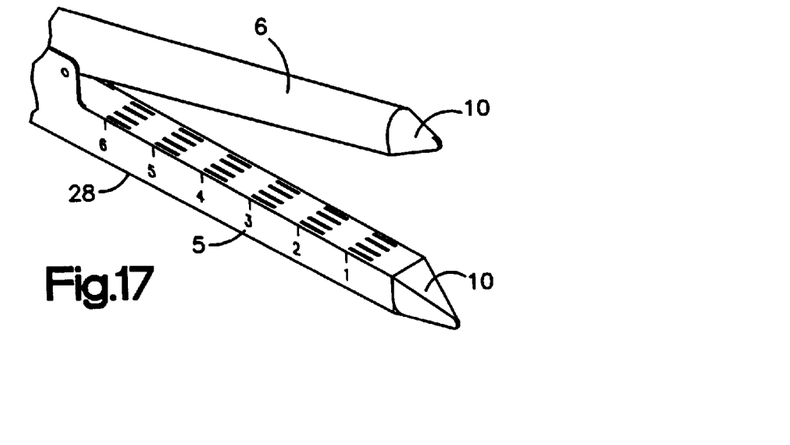
FIG. 17 shows the pericardial strip of FIG. 16 inserted on one jaw of the stapler.
Figure 18:
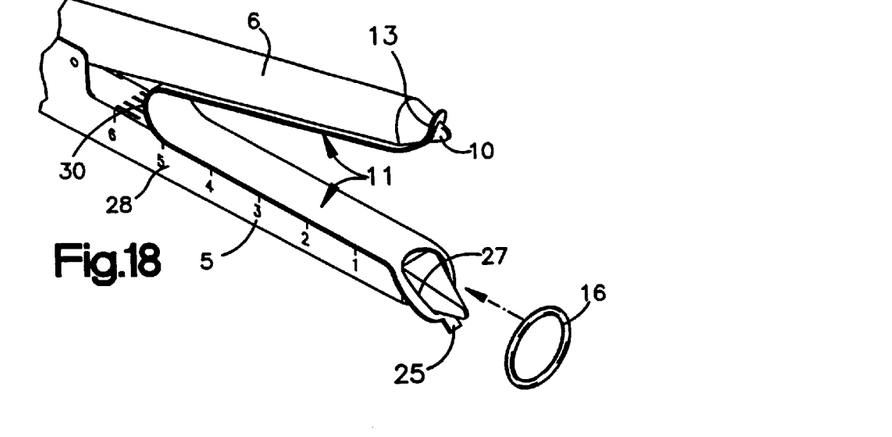
FIG. 18 is a view, similar to that of FIG. 17, with both ends of the pericardial strip of FIG. 16 on the stapler.
Figure 19:
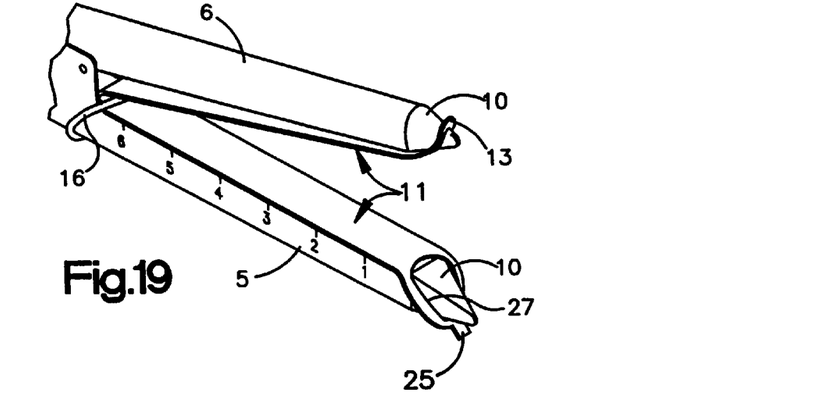
FIG. 19 is a view, similar to that of FIG. 18, with the O-ring securing the pericardial strip to the stapler.

The second embodiment of the Invention is best illustrated in FIGS. 11 to 14. Pericardial strip 11 is substantially the same as in the first embodiment at leading end 29. However, trailing end 14 is provided with hole 27, preferably of triangular shape. Hole 27 is inserted over distal end 10 of (for example) first jaw 5 and slid to proximal end 28 as shown in FIG. 13. Thereafter, opening 13 is placed over distal end 10 as shown in FIG. 14, thereby securing pericardial strip 11 to first jaw 5. A corresponding strip is placed on the second jaw in substantially the same manner. This eliminates the need for the O-ring. As in the first embodiment, tab 25 may be provided on one end of pericardial strip 11 to permit the surgeon to easily distinguish between two sizes.

The third embodiment is shown in FIGS. 16 to 19. Pericardial strip 11 is approximately twice the length of either first jaw 5 or second jaw 6. Fold 30 is provided intermediate opening 13 and hole 27. Hole 27 is inserted over distal end 10 of second jaw 6 and opening 13 is inserted over distal end 10 of first jaw 5. O-ring 16 is then slid over first jaw 5 (see FIGS. 18 and 19) to secure pericardial strip 11 on the stapler. In this form of the Invention, only one pericardial strip is required, making it easier for the surgeon to manipulate.

Although only three embodiments of the present invention have been expressly disclosed, it is, nonetheless, to be broadly construed, and not to be limited except by the character of the claims appended hereto.

What is claimed is:

1. An assembly to divide and seal visceral tissue, said assembly comprising:
    first and second strips, each of said strips having an aperture extending through said strip adjacent a leading end, an intermediate section extending from said aperture and terminating in a trailing end spaced from said leading end;
    a surgical stapler comprising an operating handle and first and second jaws mounted on said handle, said first and second jaws being movable relative to each other between open and closed positions, said first jaw having a first distal end and a first proximal end, said second jaw having a second distal end and a second proximal end, said first distal end and said second distal end being remote from said handle, said first proximal end and said second proximal end being adjacent said handle;
    said first strip being on said first jaw with said aperture thereof receiving part of said first jaw to releasably secure the leading end of said first strip to said first distal end of said first jaw, said second strip being on said second jaw with said aperture thereof receiving part of said second jaw to releasably secure the leading end of said second strip to said second distal end of said second jaw; and
    said stapler being adapted to drive said staples through said first strip, said visceral tissue, and said second strip.

2. The assembly of claim 1 wherein the leading end of said first strip is releasably secured to said first jaw adjacent said first distal end, or the leading end of said second strip is releasably secured to said second jaw adjacent said second distal end.

3. The assembly of claim 2 wherein said trailing end of each of said first strip and said second strip is releasably secured adjacent said first proximal end and said second proximal end, respectively.

4. The assembly of claim 2 wherein said trailing end is releasably secured by an O-ring.

5. The assembly of claim 2 wherein sutures are provided adjacent said trailing end of said first strip, whereby said trailing end is releasably secured to said first proximal end, said suture adapted to release after actuation of said stapler.

6. The assembly of claim 1 wherein there is more than one first strip on at least one of said first jaw and said second jaw.

7. The method of claim 1 wherein said first strip comprises a first plurality of strips, each of said first plurality of strips having an aperture extending through each respective one of said strips adjacent a leading end thereof, each said aperture being placed over said first distal end of said first jaw.

8. The method of claim 7 wherein said second strip comprises a second plurality of strips, each of said second plurality of strips having an aperture extending through each respective one of said strips adjacent a leading end thereof, each said aperture being placed over said second distal end of said second jaw.

9. The method of claim 1 wherein said visceral tissue is a lung.

10. The assembly of claim 1 wherein there is a hole adjacent said trailing end, said hole of each of said first and second strips being adjacent said first and second proximal ends, respectively, when said first strip is on said first jaw and said second strip is on said second jaw.

11. The assembly of claim 10 wherein said hole is a triangle having an apex.

12. The assembly of claim 11 wherein said apex is directed toward said trailing end.

13. The assembly of claim 1 wherein said strip is formed of a pericardial tissue material.

14. A method of dividing and sealing visceral tissue using the assembly of claim 1 comprising:
    placing of said opening of said one pericardial strip over said first distal end, placing said opening of said other pericardial strip over said second distal end, whereby said leading end of said one pericardial strip and said leading end of said other pericardial strip are releasably secured to said first jaw and said second jaw, respectively;

inserting said assembly into a body of a warm blooded animal with said tissue between said first jaw and said second jaw, actuating said stapler to drive said staples through said one pericardial strip, said visceral tissue, and said other pericardial strip;

distorting of said staples to permanently secure said one pericardial strip and said other pericardial strip to said visceral tissue; and cutting said visceral tissue adjacent said staples, and withdrawing said assembly from said body.

15. The assembly of claim 14 wherein said fold is releasably secured adjacent said handle.

16. The assembly of claim 15 wherein said fold is releasably secured by an O-ring.

17. The assembly of claim 16 wherein said O-ring is severed when said stapler is activated.

18. An assembly to divide and seal visceral tissue, said assembly comprising:

a strip having a first aperture extending through said strip adjacent a leading end thereof, said strip having an intermediate section extending from said first aperture and terminating in a trailing end spaced from said leading end, a second aperture extending through said strip adjacent said trailing end;

a surgical stapler comprising an operating handle and first and second jaws mounted on said handle, said first and second jaws being movable relative to each other between open and closed positions, said first jaw having a first distal end and a first proximal end, said second jaw having a second distal end and a second proximal end, said first distal end and said second distal end being remote from said handle, said first proximal end and said second proximal end being adjacent said handle;

said first distal end of said first jaw projecting into said first aperture and said second distal end of said second jaw projecting into said second aperture, a fold being formed in said intermediate section of said strip adjacent said handle, such that said stapler is operative to drive staples through a first length of said strip between said fold and said first aperture, visceral tissue located between said first and second jaws, and a second length of said strip between said fold and said second aperture.

19. The method of claim 18 wherein an O-ring is slipped over said first jaw or said second jaw and slid adjacent said handle, thereby releasably securing said fold.

20. The method of claim 1 wherein there is a plurality of strips, each of said plurality of strips having a first aperture extending through each respective one of said strips adjacent a leading end thereof and a second aperture extending through each respective strip adjacent a trailing end thereof, said method comprising placing one of each said first and second apertures over said first distal end, and placing the other one of each respective said first and second aperture over said second distal end.

21. A method of dividing and sealing visceral tissue using the assembly of claim 18 comprising:

placing said first or second aperture over said first distal end, placing another of said first or second aperture over said second distal end, and releasably securing said fold adjacent said handle;

inserting said assembly into a body of a warm blooded animal with said tissue between said first jaw and said second jaw, actuating said stapler to drive said staples through said first length of said strip, said visceral tissue, and said second length of said strip;

distorting said staples to permanently secure said strip to said visceral tissue; and cutting said visceral tissue adjacent said staples, and withdrawing said assembly from said body.

22. The assembly of claim 18 wherein said strip is formed of a pericardial tissue material.

23. A strip for use with a surgical stapler for dividing and sealing visceral tissue, said strip comprising an elongated sheet having an aperture extending through said sheet adjacent a leading end thereof, said aperture being dimensioned for receiving a jaw of a surgical stapler, said sheet having an intermediate section extending from said aperture and terminating in a trailing end spaced from said leading end.

24. The strip of claim 23 wherein said strip is formed of a pericardial tissue material.

25. The strip of claim 24 further including means for releasably securing said trailing end of said sheet relative to the jaw of the surgical stapler.

26. The strip of claim 24 wherein said means for releasably securing is a hole formed through said sheet adjacent said trailing end, said hole being dimensioned for receiving a jaw of the surgical stapler.

27. The strip of claim 24 wherein said means for releasably securing is an O-ring adapted for positioning over said strip and a jaw of the surgical stapler.

28. A strip for use with a surgical stapler for dividing and sealing visceral tissue, said strip comprising an elongated sheet having a first aperture extending through said sheet adjacent a leading end thereof, an intermediate portion extending from said aperture and terminating in a trailing end spaced from said leading end, a second aperture extending through said sheet adjacent said trailing end, each of said first and second apertures being dimensioned for receiving part of a jaw of the surgical stapler.

29. The strip of claim 28 wherein said strip is formed of a pericardial tissue material.

30. The strip of claim 28 wherein said second aperture is triangular.

31. The strip of claim 28 wherein a fold is formed in said intermediate portion of said strip adjacent a handle of the surgical stapler when said strip is on the jaws of the surgical stapler and the end part of the one jaw is received in said second aperture and the end part of the other jaw is received in said aperture, said strip further including means for releasably securing said fold relative to the handle of the surgical stapler.

* * * * *

UNITED STATES PATENT AND TRADEMARK OFFICE
CERTIFICATE OF CORRECTION

PATENT NO.   : 6,099,551
DATED        : August 8, 2000
INVENTOR(S)  : Shlomo Gabbay It is certified that error appears in the above-identified patent and that said Letters Patent is hereby corrected as shown below:

Delete claims 1-31 and substitute new claims 1-31:

1. An assembly to divide and seal visceral tissue, said assembly comprising:

first and second strips, each of said strips having an aperture extending through said strip adjacent a leading end, an intermediate section extending from said aperture and terminating in a trailing end spaced from said leading end;

a surgical stapler comprising an operating handle and first and second jaws mounted on said handle, said first and second jaws being movable relative to each other between open and closed positions, said first jaw having a first distal end *and* a first proximal end, said second jaw having a second distal end and a second proximal end, said first distal end and said second distal end being remote from said handle, said first proximal end and said second proximal end being adjacent said handle;

said first strip being on said first jaw with said aperture thereof receiving part of said first jaw to releasably secure the leading end of said first strip to said first distal end of said first jaw, said second strip being on said second jaw with said aperture thereof receiving part of said second jaw to releasably secure the leading end of said second strip to said second distal end of said second jaw; and said stapler being adapted to drive said staples through said first strip, said visceral tissue, and said second strip.

2. The assembly of claim 1 wherein the leading end of said first strip is releasably secured to said first jaw adjacent said first distal end, or the leading end of said second strip is releasably secured to said second jaw adjacent said second distal end.

UNITED STATES PATENT AND TRADEMARK OFFICE
CERTIFICATE OF CORRECTION

PATENT NO. : 6,099,551
DATED : August 8, 2000
INVENTOR(S) : Shlomo Gabbay

It is certified that error appears in the above-identified patent and that said Letters Patent is hereby corrected as shown below:

3. The assembly of claim 2 wherein said trailing end of each of said first strip and said second strip is releasably secured adjacent said first proximal end and said second proximal end, respectively.

4. The assembly of claim 2 wherein said trailing end is releasably secured by an 0-ring.

5. The assembly of claim 2 Wherein sutures are provided adjacent said trailing end of said first strip, whereby said trailing end is releasably secured to said first proximal end, said suture adapted to release after actuation of said stapler.

6. The assembly of claim 1 wherein there is more than one first strip on at least one of said first jaw and said second jaw.

7. The assembly of claim 1 wherein there is a hole adjacent said trailing end, said hole of each of said first and second strips being adjacent said first and second proximal ends, respectively, when said first strip is on said first jaw and said second strip is on said second jaw.

8. The assembly of claim 7 wherein said hole is a triangle having an apex.

9. The assembly of claim 8 wherein said apex is directed toward said trailing end.

10. The assembly of claim 1 wherein said strip is formed of a pericardial tissue material.

UNITED STATES PATENT AND TRADEMARK OFFICE
CERTIFICATE OF CORRECTION

PATENT NO. : 6,099,551
DATED : August 8, 2000
INVENTOR(S) : Shlomo Gabbay

It is certified that error appears in the above-identified patent and that said Letters Patent is hereby corrected as shown below:

11. A method of dividing and sealing visceral tissue using the assembly of claim 1 comprising:

placing of said opening of said one pericardial-strip over said first distal end, placing said opening of said other pericardial strip over said second distal end, whereby said leading end of said one pericardial strip and said leading end of said other pericardial strip are releasably secured to said first jaw and said second jaw, respectively;

inserting said assembly into a body of a warm blooded animal with said tissue between said first jaw and said second jaw, actuating said stapler to drive said staples through said one pericardial strip, said visceral tissue, and said other pericardial strip;

distorting of said staples to permanently secure said one pericardial strip and said other pericardial strip to said visceral tissue; and cutting said visceral tissue adjacent said staples, and withdrawing said assembly from said body.

12. The method of claim 11 wherein said first strip comprises a first plurality of strips, each of said first plurality of strips having an aperture extending through each respective one of said strips adjacent a leading end thereof, each said aperture being placed over said first distal end of said first jaw.

13. The method of claim 12 wherein said second strip comprises a second plurality of strips, each of said second plurality of strips having an aperture extending through each respective one of said strips adjacent a leading end thereof, each said aperture being placed over said second distal end of said second jaw.

14. The method of claim 11 wherein said visceral tissue is a lung.

UNITED STATES PATENT AND TRADEMARK OFFICE
CERTIFICATE OF CORRECTION

PATENT NO.   : 6,099,551
DATED        : August 8, 2000
INVENTOR(S)  : Shlomo Gabbay It is certified that error appears in the above-identified patent and that said Letters Patent is hereby corrected as shown below:

15. An assembly to divide and seal visceral tissue, said assembly comprising:

a strip having a first aperture extending through said strip adjacent a leading end thereof, said strip having an intermediate section extending from said first aperture and terminating in a trailing end spaced from said leading end, a second aperture extending through said strip adjacent said trailing end;

a surgical stapler comprising an operating handle and first and second jaws mounted on said handle., said first and second jaws being movable relative to each other between open and closed positions, said first jaw having a first distal end and a first proximal end, said second jaw having a second distal end and a second proximal end, said first distal end and said second distal end being remote from said handle, said first proximal end and said second proximal end being adjacent said handle; said first distal end of said first jaw projecting into said first aperture and said second distal end of said second jaw projecting into said second aperture, a fold being formed in said intermediate section of said strip adjacent said handle, such that said stapler is operative to drive staples through a first length of said strip between said fold and said first aperture, visceral tissue located between said first and second jaws, and a second length of said strip between said fold and said second aperture.

16. The assembly of claim 15 wherein said fold is releasably secured adjacent said handle.

17. The assembly of claim 16 wherein said fold is releasably secured by an 0-ring.

18. The assembly of claim 17 wherein said 0-ring is severed when said stapler is activated.

UNITED STATES PATENT AND TRADEMARK OFFICE
CERTIFICATE OF CORRECTION

PATENT NO. : 6,099,551
DATED : August 8, 2000
INVENTOR(S) : Shlomo Gabbay

It is certified that error appears in the above-identified patent and that said Letters Patent is hereby corrected as shown below:

19. The assembly of claim 15 wherein said strip is formed of a pericardial tissue material, 20. A method of dividing and sealing visceral tissue using the assembly of claim 15 comprising:

placing said first or second aperture over said first distal end, placing another of said first or second aperture over said second distal end, and releasably securing said fold adjacent said handle:

inserting said assembly into a body of a warm blooded animal with said tissue between said first jaw and said second jaw, actuating said stapler to drive said staples through said first length of said strip, said visceral tissue, and said second length of said strip;

distorting said staples to permanently secure said strip to said visceral tissue: and cutting said visceral tissue adjacent said staples, and withdrawing said assembly from said body.

21. The method of claim 20 wherein an O-ring is slipped over said first jaw or said second jaw and slid adjacent said handle, thereby releasably securing said fold.

22. The method of claim 20 wherein there is a plurality of strips, each of said plurality of strips . having a first aperture extending through each respective one of said strips adjacent a leading end thereof and a second aperture extending through each respective strip adjacent a trailing end thereof, said method comprising placing one of each said first and second apertures-over said first distal end, and placing the other one of each respective said first and second aperture over said second distal end.

UNITED STATES PATENT AND TRADEMARK OFFICE
CERTIFICATE OF CORRECTION

PATENT NO. : 6,099,551
DATED : August 8, 2000
INVENTOR(S) : Shlomo Gabbay

It is certified that error appears in the above-identified patent and that said Letters Patent is hereby corrected as shown below:

23. A strip for use with a surgical stapler for dividing and sealing visceral tissue, said strip comprising an elongated sheet having an aperture extending through said sheet adjacent a leading end thereof, said aperture being dimensioned for receiving a jaw of a surgical stapler, said sheet having an intermediate section extending from said aperture and terminating in a trailing end spaced from said leading end.

24. The strip of claim 23 wherein said strip is formed of a pericardial tissue material.

25. The strip of claim 24 further including means for releasably securing said trailing end of said sheet relative to the jaw of the surgical stapler.

26. The strip of claim 24 wherein said means "for releasably securing is a hole formed through said sheet adjacent said trailing end, said hole being dimensioned for receiving a jaw of the surgical stapler.

27. The strip of claim 24 wherein said means for releasably securing is an 0-ring adapted for positioning over said strip and a jaw of the surgical stapler.

28. A strip for use with a surgical stapler for dividing and sealing visceral tissue, said strip comprising an elongated sheet having a first aperture extending through said sheet adjacent a leading end thereof, an intermediate portion extending from said aperture and terminating in a trailing end spaced from said leading end, a second aperture extending through said sheet adjacent said trailing end, each of said first and second apertures being dimensioned for receiving part of a jaw of the surgical stapler.

UNITED STATES PATENT AND TRADEMARK OFFICE
CERTIFICATE OF CORRECTION

PATENT NO. : 6,099,551
DATED : August 8, 2000
INVENTOR(S) : Shlomo Gabbay

It is certified that error appears in the above-identified patent and that said Letters Patent is hereby corrected as shown below:

29. The strip of claim 28 wherein said strip is formed of a pericardial tissue material.

30. The strip of claim 28 wherein said second aperture is triangular.

31. The strip of claim 28 wherein a fold is formed in said intermediate portion of said strip adjacent a handle of the surgical stapler when said strip is on the jaws of the surgical stapler and the end part of the one jaw is received in said second aperture and the end part of the other jaw is received in said aperture, said strip further including means for releasably securing said fold relative to the handle of the surgical stapler.

Signed and Sealed this

Fourteenth Day of August, 2001

*Attest:*

*Attesting Officer*

NICHOLAS P. GODICI
*Acting Director of the United States Patent and Trademark Office*